US012576175B2

(12) United States Patent  
Verhoeven et al.

(10) Patent No.: US 12,576,175 B2  
(45) Date of Patent: Mar. 17, 2026

(54) METHOD AND DEVICE FOR STERILIZING MEDICAL INSTRUMENTS USING A PLASMA

(71) Applicant: Log10 B.V., Eindhoven (NL)

(72) Inventors: Franciscus Maria Verhoeven, Amsterdam (NL); Theo Alex Eduard Van Der Leij, Moergestel (NL); Mirte Peeters, Dongen (NL); Thijs De Jong, De Bilt (NL)

(73) Assignee: LOG10 B.V., Eindhoven (NL)

( * ) Notice: Subject to any disclaimer, the term of this patent is extended or adjusted under 35 U.S.C. 154(b) by 589 days.

(21) Appl. No.: 17/909,922

(22) PCT Filed: Mar. 12, 2021

(86) PCT No.: PCT/NL2021/050169  
§ 371 (c)(1),  
(2) Date: Sep. 7, 2022

(87) PCT Pub. No.: WO2021/182959  
PCT Pub. Date: Sep. 16, 2021

(65) Prior Publication Data  
US 2023/0293748 A1 Sep. 21, 2023

(30) Foreign Application Priority Data  
Mar. 12, 2020 (NL) ...................................... 2025108

(51) Int. Cl.  
*A61L 2/00* (2006.01)  
*A61L 2/14* (2006.01)  
(Continued)

(52) U.S. Cl.  
CPC ........... *A61L 2/14* (2013.01); *A61L 2202/122* (2013.01); *A61L 2202/123* (2013.01); (Continued)

(58) Field of Classification Search  
CPC ... A61L 2/00; A61L 2/20; A61L 11/00; A61L 2/202; A61L 2/24; A61L 2/0094  
(Continued)

(56) References Cited

U.S. PATENT DOCUMENTS 5,069,880 A 12/1991 Karlson  
5,115,166 A * 5/1992 Campbell ................ H05H 1/46  
422/23

(Continued)

FOREIGN PATENT DOCUMENTS

EP 0387022 A2 9/1990  
EP 3228550 A1 10/2017  
(Continued)

OTHER PUBLICATIONS

International Search Report dated May 19, 2021, issued in corresponding International Application No. PCT/NL2021/050169 (3 pgs.).

(Continued)

*Primary Examiner* — Monzer R Chorbaji  
(74) *Attorney, Agent, or Firm* — Pillsbury Winthrop Shaw Pittman, LLP

(57) ABSTRACT

A device and method for sterilizing one or more medical instruments. The device includes a sterilizing chamber for holding the medical instruments to be sterilized, a pressure reducer for selectively reducing the pressure in the chamber, an atmospheric or superatmospheric plasma source for providing a sterilizing mixture, and a duct for guiding the sterilizing mixture from the plasma source to the sterilizing chamber. The duct includes a choke arranged for causing a choked flow of the sterilizing mixture from the plasma source to the chamber when the chamber is at the reduced pressure for preventing pressure drop in the plasma source.

12 Claims, 5 Drawing Sheets

(51) Int. Cl.
  *A61L 9/00* (2006.01)
  *B01J 19/08* (2006.01)
(52) U.S. Cl.
  CPC ....... *A61L 2202/14* (2013.01); *A61L 2202/15*
    (2013.01); *A61L 2202/24* (2013.01)
(58) Field of Classification Search
  USPC ........................ 422/22, 186.05, 186.21, 305
  See application file for complete search history.

(56) References Cited

U.S. PATENT DOCUMENTS

| | | | |
|---|---|---|---|
| 8,062,590 B1 | 11/2011 | Ricciardi et al. | |
| 2010/0196198 A1 | 8/2010 | Legube | |
| 2011/0027125 A1* | 2/2011 | Golkowski | ............. A61L 11/00 |
| | | | 422/186.21 |

FOREIGN PATENT DOCUMENTS

| | | |
|---|---|---|
| JP | 2017-051555 A | 3/2017 |
| WO | 2011099935 A1 | 8/2011 |

OTHER PUBLICATIONS

Written Opinion of the International Searching Authority dated May 19, 2021, issued in corresponding International Application No. PCT/NL2021/050169 (5 pgs.).
S. Moreau et al., "Using the Flowing Afterglow of a Plasma to Inactivate Bacillus Subtilis Spores: Influence of the Operating Conditions", Journal of Applied Physics, vol. 88, No. 2, Jul. 15, 2000, pp. 1166-1174.

\* cited by examiner

100

102
Supply air stream to
plasma source

104
Ionize air

106
Block chamber for
sterilizing mixture

108
Reduce pressure in
chamber

110
Supply air stream to
chamber via choke

112
Sterilizing agent
(partially) condenses
on instrument

114
Open bypass

116
Take instrument
from chamber

METHOD AND DEVICE FOR STERILIZING MEDICAL INSTRUMENTS USING A PLASMA

CROSS-REFERENCE TO RELATED APPLICATIONS

This application is the U.S. National Stage of PCT/NL2021/050169, filed Mar. 12, 2021, which claims priority to Netherlands Patent Application No. 2025108, filed Mar. 12, 2020, the contents of each of which are incorporated herein by reference in their entireties.

FIELD OF THE INVENTION

The present invention relates to sterilizing medical instruments, such as dental instruments using a plasma.

BACKGROUND TO THE INVENTION

Reusable medical instruments are instruments that health care providers can reuse to diagnose and/or treat multiple patients. Examples of reusable medical instruments include medical instruments used in dental care, such as scalpels, syringes, scopes, mirrors, drills, burs, discs, handpieces, excavators, turbines, files, reamers, etc.

When used on patients, reusable instruments become soiled and contaminated with blood, tissue and other biological debris such as microorganisms. To avoid any risk of infection by a contaminated instrument, the reusable instruments can be sterilized. Sterilizing results in a medical instrument that can be safely used more than once in the same patient, or in more than one patient. Adequate sterilizing of reusable medical instruments is vital to protecting patient safety.

Various sterilizing agents can be used for sterilizing medical instruments. Historically, steam or hydrogen peroxide is often used. More recently, plasma devices are being used for ionizing gases or gas mixtures, the ionized gas being used as sterilizing agent. Electrons in the plasma impact on gas molecules causing dissociation and ionization of these molecules, which creates a mix of reactive species. It is known to directly expose the medical instruments to the plasma, or to expose the medical instruments to the (partially) recombined plasma, sometimes referred to as afterglow, see e.g. S. Moreau et al., "Using the flowing afterglow of a plasma to inactivate *Bacillus subtilis* spores: Influence of the operating conditions", J. Appl. Phys. Vol. 88, No. 2, 15 Jul. 2000.

Several attempts have been made to improve upon plasma sterilizing. US2011/0027125A1 discloses a system comprising a chamber and a plasma generator for generating free radicals combined with use of a hydrogen peroxide solution.

It is also known to use an atmospheric or superatmospheric plasma source.

Plasma sources can have the disadvantage that the composition of the sterilizing agent, produced by generating an at least partially ionized gas mixture, can vary significantly with varying temperature and or pressure of the plasma.

SUMMARY OF THE INVENTION

It is an object to provide a method and system for sterilizing medical instruments, such as dental instruments. More in particular, it is an object to provide a device and method for sterilizing one or more medical instruments, such as dental instruments, using a plasma source, wherein the composition of the sterilizing agent can be kept constant. An object is to provide a device and method for sterilizing one or more medical instruments, such as dental instruments, using a plasma source, wherein the composition of the sterilizing agent varies less than in prior art arrangements.

When using a plasma source, e.g. an atmospheric or superatmospheric plasma source, it can be desired to be able to reduce a pressure in a treatment chamber for the medical instruments to below the pressure in the plasma source. The pressure can e.g. be reduced for emptying the chamber of ambient air that entered the chamber while loading the medical instrument or instruments to be treated, prior to having the plasma or at least partially recombined gas mixture from the plasma source enter the treatment chamber. The pressure can also e.g. be reduced for effectively drawing the at least partially recombined gas mixture from the plasma source into the treatment chamber. As already explained, reducing the pressure in the plasma source can undesiredly change the composition of the at least partially recombined gas mixture from the plasma source.

Thereto, according to an aspect is provided a device for sterilizing one or more medical instruments. The device includes a sterilizing chamber for holding the medical instrument or a plurality of medical instruments to be sterilized. The device includes a plasma source, such as an atmospheric or superatmospheric plasma source, for providing a sterilizing mixture to the medical instrument(s) in the chamber. The plasma source can be arranged for feeding a gas stream, such as an, e.g. humidified, air stream through the plasma source and at least partially ionizing the gas stream to form the sterilizing mixture. The device includes a duct for guiding the sterilizing mixture from the plasma source to the sterilizing chamber. The device includes a pressure reducer for selectively reducing the pressure in the chamber to below the pressure in the plasma source. The duct includes a choke. The choke is arranged for causing a choked flow of the sterilizing mixture from the plasma source to the chamber when the chamber is at the reduced pressure.

The choked flow is a fluid dynamic condition associated with the Venturi effect. When a gas stream at a given pressure and temperature passes through a choke, also referred to as restriction or constriction, into a lower pressure environment the gas velocity increases. At initially subsonic upstream conditions, the conservation of mass principle requires the gas velocity to increase as it flows through the smaller cross-sectional area of the choke. At the same time, the Venturi effect causes the static pressure, and therefore the density, to decrease at the choke. Choked flow is a limiting condition where the mass flow will not increase with a further decrease in the downstream pressure for a fixed upstream pressure and temperature. The physical point at which the choking occurs for adiabatic conditions, is when the velocity at the exit of the choke is at sonic conditions; i.e., at a Mach number of 1. Hence, thanks to the choke the pressure in the plasma source does not decrease below a predetermined threshold pressure when the pressure in the chamber is reduced further below such predetermined threshold pressure.

Steady-state choked flow occurs when the pressure downstream of the choke falls below a critical value relative to the pressure upstream of the choke. The critical pressure value $p^*$ can be calculated from the following equation.

$$\frac{p^*}{p_0} = \left(\frac{2}{\gamma+1}\right)^{\frac{\gamma}{\gamma-1}}$$

Herein $p_0$ is the absolute upstream pressure and $\gamma$ the heat capacity ratio $c_p/c_v$ of the gas or gas mixture. For air the heat capacity ratio $\gamma$ is about 1.4. Thus for air $p^*=0.528p_0$.

When the gas velocity is choked, the equation for the mass flow rate is as follows.

$$\dot{m} = C_d A \sqrt{\gamma \rho_0 p_0 \left(\frac{2}{\gamma+1}\right)^{\frac{\gamma+1}{\gamma-1}}}$$

Herein $\dot{m}$ is the mass flow rate in kg/m2, $C_d$ the discharge coefficient (dimensionless), A the cross-sectional area of the hole in $m^2$, $\rho_0$ the real gas density at total pressure $p_0$ and temperature $T_0$ in $kg/m^3$, and $T_0$ the absolute upstream temperature of the gas or gas mixture in K. The discharge coefficient $C_d$ is the ratio of the actual discharge to the theoretical discharge, i.e. the ratio of the mass flow rate at the discharge end of the nozzle to that of an ideal nozzle which expands an identical working fluid from the same initial conditions to the same exit pressures. The discharge coefficient $C_d$ is generally in the range of 0.5-1. The Discharge coefficient can e.g. be on the order of 0.6 (e.g. sharp edged orifice) to 0.8 (e.g. longer hole). The discharge coefficient for a specific choke can easily be determined by comparing a measured mass flow rate to the theoretical mass flow rate ($C_d=1$).

Hence, by properly designing the flow restriction properties of the choke it is possible to prevent the pressure in the plasma source to decrease below the threshold pressure, while the sterilizing chamber is evacuated. Thus, the plasma source can be operated continuously at nearly constant pressure, e.g. at near-ambient pressure. Hence, composition of the at least partially recombined gas mixture from the plasma source can remain constant, or at least nearly constant, i.e. sufficiently constant, despite reducing the pressure in the sterilizing chamber.

According to an aspect is provided a method for sterilizing one or more medical instruments. The method includes providing the medical instrument(s) to be sterilized in a sterilizing chamber. The method includes providing a plasma source, such as an atmospheric or superatmospheric plasma source, for providing a sterilizing mixture. The method includes guiding the sterilizing mixture from the plasma source to the sterilizing chamber through a duct. The method includes preventing the pressure in the plasma source to reduce below a predetermined threshold pressure by choking the flow of sterilizing mixture from the plasma source to the chamber. As explained, preventing the pressure in the plasma source to be reduced below the predetermined threshold pressure can aid in keeping the composition of the at least partially recombined gas mixture from the plasma source constant, or at least nearly constant.

The method can include reducing the pressure in the sterilizing chamber, e.g. by means of a pressure reducer, such as a pump. Optionally, the pressure in the sterilizing chamber is reduced while preventing the sterilizing mixture from entering the sterilizing chamber. Thereto the device can include a valve in the duct for closing the duct. Thus, the reduced pressure in the chamber is realized, while removing at least part of the gas (mixture) present in the chamber e.g. upon loading of the medical instrument(s) into the chamber.

Also, the reduced pressure allows for efficient and/or effective distribution of the sterilizing mixture around and onto the medical instrument(s) to be sterilized. Reducing of the pressure in the sterilizing chamber can be stopped, e.g. before, upon or during the sterilizing mixture entering the sterilizing chamber. Stopping pressure reduction can e.g. be achieved by stopping the pump or closing a valve in a duct between the pump and the sterilizing chamber.

While preventing the sterilizing mixture to enter the chamber, the sterilizing mixture may be fed to a destructor arranged for destructing airborne components exiting from the chamber. The device can include a removal duct from the plasma source to the destructor. The removal duct can include a valve for selectively opening or closing the removal duct. Hence, the plasma source can be operated continuously. The sterilizing mixture can be fed to the chamber when needed, and fed to the destructor when not needed in the chamber. Thus, the plasma source is immediately ready for providing the sterilizing mixture to the chamber when required.

Optionally, the method includes, after reducing the pressure in the chamber, allowing the pressure in the chamber to rise by feeding the sterilizing mixture into the chamber via a choke. Thus, the pressure in the chamber can be raised by feeding the sterilizing mixture into the chamber, while at the same time preventing the pressure in the plasma source to be below the predetermined threshold pressure.

Optionally, the method includes, when the pressure in the chamber exceeds a predetermined threshold opening pressure (such as the predetermined threshold pressure), opening a bypass duct from the plasma source to the chamber. Hence greater mass flow of the sterilizing mixture can be allowed without negatively affecting pressure conditions of the plasma source. Thereto, the device can include a bypass duct, bypassing the choke. The bypass duct can include a bypass valve for being opened when a pressure difference between the chamber and the plasma source is below a predetermined threshold value. The bypass valve can be opened when the pressure in the chamber is above the predetermined threshold opening pressure, e.g. above the predetermined threshold pressure. Hence, when the pressure in the chamber is not too low, i.e. not below the predetermined threshold opening pressure, the bypass valve can be opened to allow a greater mass flow of sterilizing mixture than is achievable through the choke. As the pressure in the chamber is above the threshold opening pressure, the plasma source need not be protected by the choke.

Optionally, the device includes a pressure sensor for determining the pressure in the chamber. The device can include a controller. The controller can be arranged for automatically opening the bypass valve when the pressure inside the chamber, as e.g. determined by the pressure sensor, is above the threshold opening pressure. The controller can be arranged for automatically opening the bypass valve when the pressure difference between the plasma source and the chamber is below the threshold value.

It will be appreciated that any of the aspects, features and options described in view of the method apply equally to the device. It will also be clear that any one or more of the above aspects, features and options can be combined.

BRIEF DESCRIPTION OF THE DRAWINGS

Embodiments of the present invention will now be described in detail with reference to the accompanying drawings in which.

DETAILED DESCRIPTION

Figure 1:
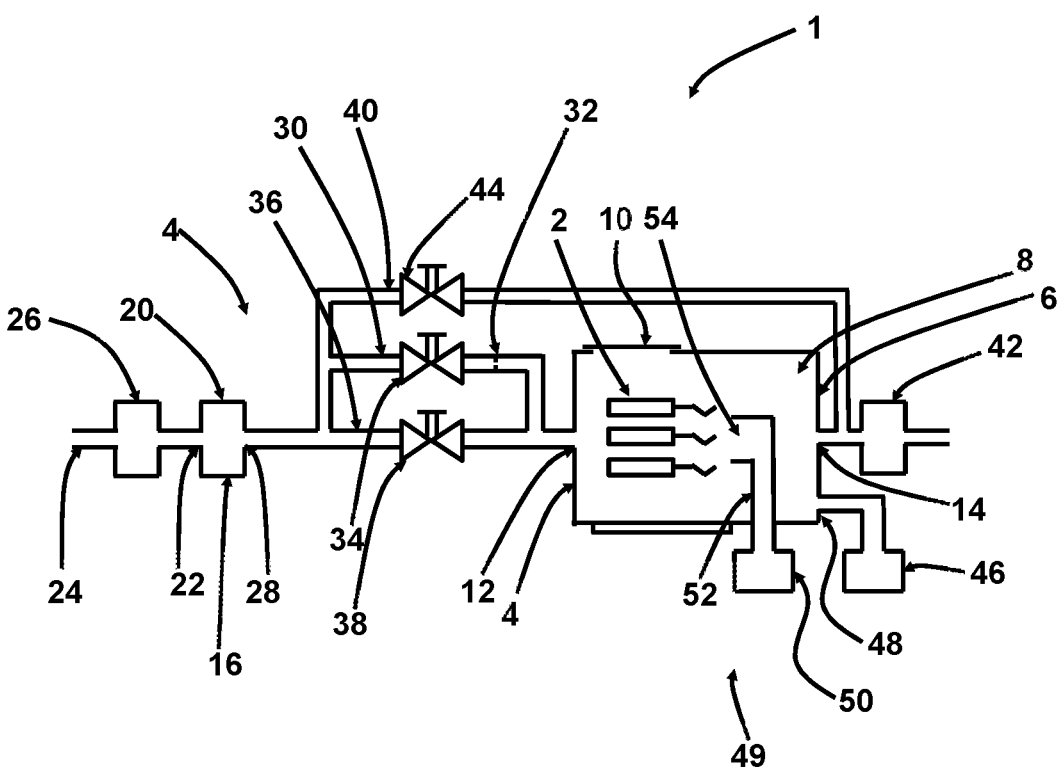
FIG. 1 shows a schematic representation of an example of an apparatus for sterilizing a medical instrument.

FIG. 1 shows a schematic representation of an example of an apparatus 1 for sterilizing a medical instrument 2. The apparatus 1 includes a sterilizing chamber 4. The sterilizing chamber 4 is arranged for placing the medical instrument 2 to be sterilized therein. In this example, the chamber 4 is arranged for placing a plurality of medical instruments 2 to be sterilized therein. Here, the medical instruments 2 are dental instruments. The chamber 4 includes walls 6 forming an internal space 8 for receiving the medical instruments 2. In this example, the chamber 4 has a door 10 for allowing the medical instruments 2 to be inserted into and extracted from the internal space 8 of the chamber 4. The chamber 4 includes a sterilizing agent supply port 12. The chamber 4 includes an exhaust port 14.

The apparatus 1 includes a sterilizing agent source 16. The sterilizing agent source 16 is arranged for providing a sterilizing agent. The sterilizing agent includes recombined ionized humidified air. In this example, the sterilizing agent source 16 includes a plasma source 20. The plasma source 20 includes an input port 22 for feeding a humidified air stream into the plasma source 20. In FIG. 1 the input port 22 is connected to an air stream supply 24 via a humidifier 26. The plasma source 20 includes an output port 28 in communication with the sterilizing agent supply port 12 of the chamber 4.

A first duct 30 extends between the plasma source 20 output port 28 and the sterilizing agent supply port 12 of the chamber 4. The first duct includes a choke 32. In this example, the first duct 20 further includes a first valve 34. The first valve 34 is arranged for selectively opening and closing the first duct 30. Here the first valve 34 is positioned upstream of the choke 32. It will be clear that alternatively the first valve 34 may be positioned downstream of the choke 32.

In the example of FIG. 1 a second duct 36 extends between the plasma output port 28 and the sterilizing agent supply port 12 of the chamber 4. The second duct 36 includes a second valve 38. The second valve 38 is arranged for selectively opening and closing the second duct 36.

In the example of FIG. 1 a third duct 40 extends between the plasma output port 28 and a destructor 42. The destructor 42 is arranged for destructing airborne components. In this example, the third duct 40 further includes a third valve 44. The third valve 44 is arranged for selectively opening and closing the third duct 40. In FIG. 1 the destructor 42 is further connected to the exhaust port 14 of the chamber 4 for destructing any contaminants carried by the exhausted sterilizing agent.

In this example, a pump 46 is connected to a pumping port 48 of the chamber 4. The apparatus 1 in this example includes a temperature control unit 49. In this example, the temperature control unit 49 includes a cooling unit 50. The cooling unit 50 is arranged for cooling the medical instruments 2. In FIG. 1, the cooling unit 50 is arranged for cooling the instruments 2 prior to placing the instruments 2 in the chamber 4. The cooling unit 50 in this example includes a gas conduit 52 for cooling the medical instrument using a gas, here air. The gas conduit 52 includes a mouth 54, here nozzles, pointing a stream of the gas onto the medical instrument 2.

Figure 2:
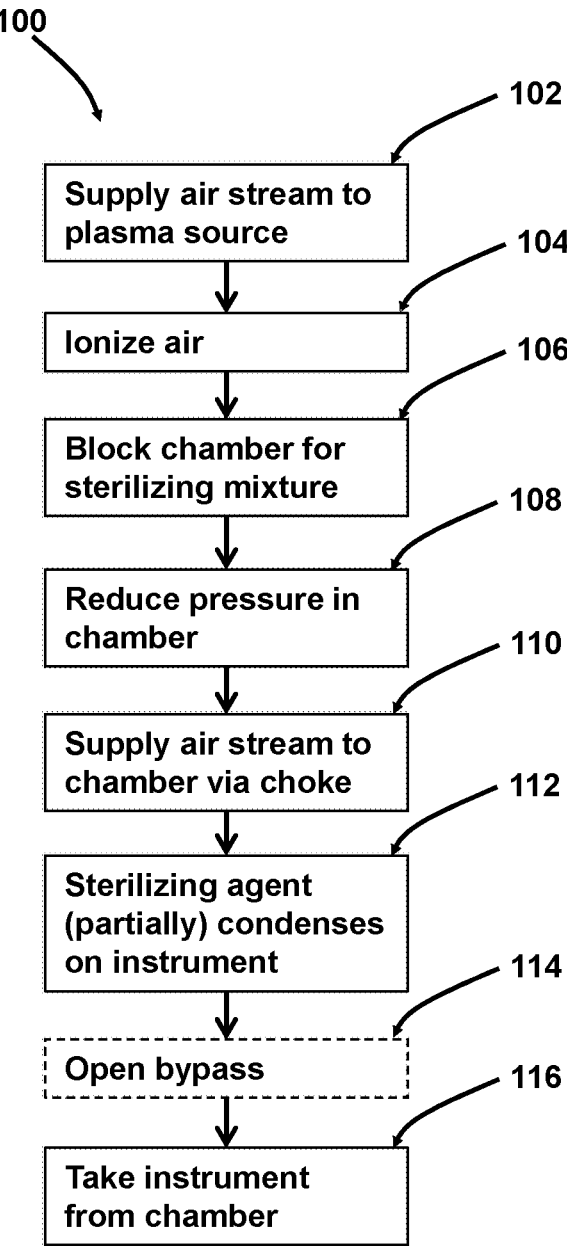
FIG. 2 shows a schematic representation of a method.

The apparatus as described in relation to FIG. 1 can be used in the following exemplary method 100, see FIG. 2. An air stream is supplied 102 to the input port 22 of the plasma source 20 via the humidifier 26. Depending on the humidity of the air supplied to the humidifier 26, the humidifier 26 can add or remove water from the air such that at the exit of the humidifier 26 an air stream with a predetermined humidity is obtained. In this example, the air stream entering the plasma source 20 has a predetermined specific humidity, SH. The specific humidity of the air entering the plasma source 20 can e.g. be 10±1 g/kg (grams of water per kg of air). In the plasma source 20 the air is ionized 104. The ionized air is fed to the output port 28.

With the first and second valves 34, 38 closed, preventing 106 the sterilizing mixture to enter the chamber 4, the sterilizing mixture may be fed to the destructor 42 via the third duct 40 with the third valve 44 opened. Hence, the plasma source 20 can be operated continuously. The sterilizing mixture can be fed to the chamber 4 when needed, and fed to the destructor 42 when not needed in the chamber 4. Thus, the plasma source 20 is immediately ready for providing the sterilizing mixture 18 to the chamber 4 when required.

Figure 3:
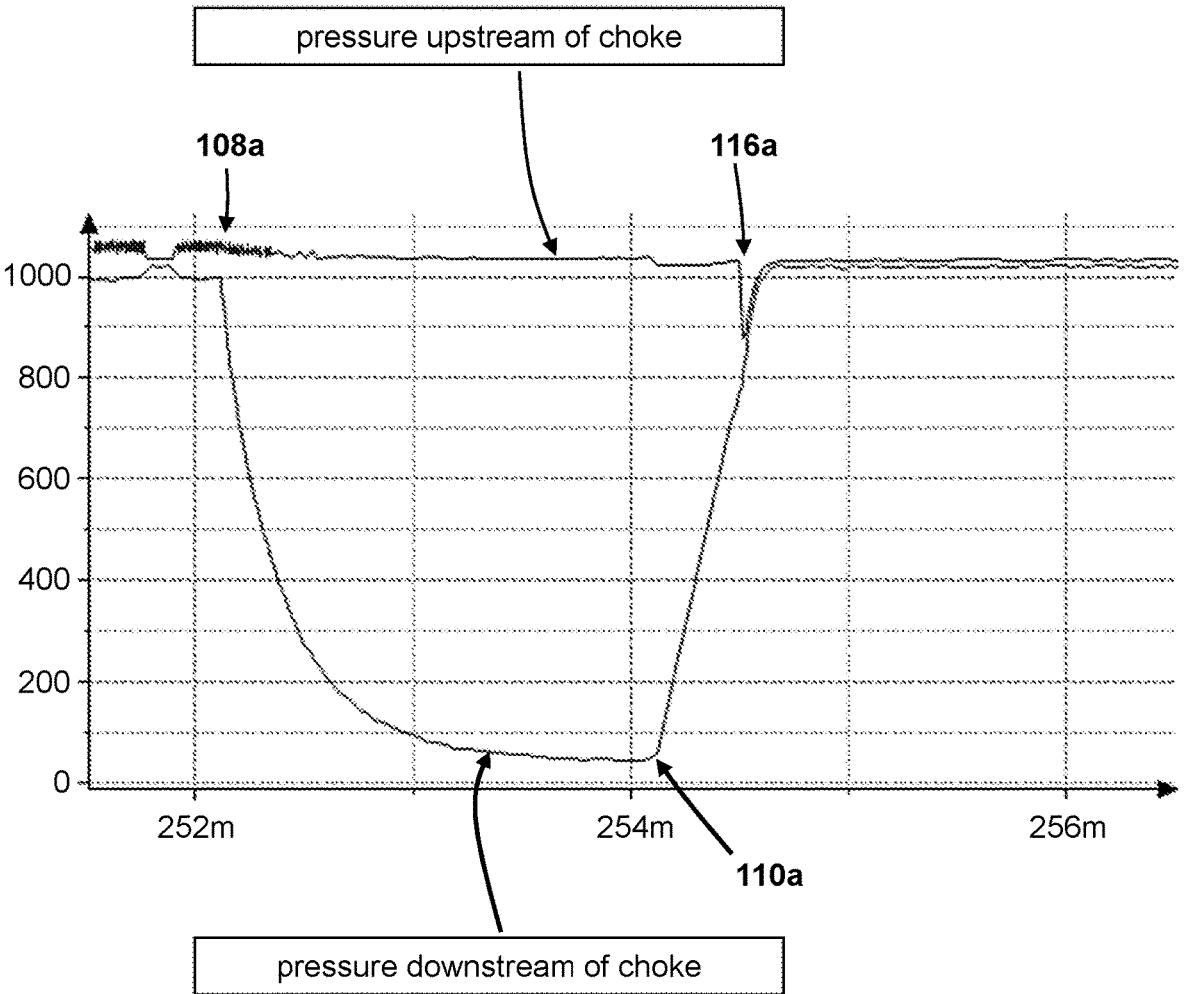
FIG. 3 shows an example of pressure curves.

The medical instruments 2 to be sterilized are placed inside the chamber 4. Then, the pressure in the chamber 4 is reduced 108 by the pump 46. In this example the pressure is reduced to approximately 50 mbar FIG. 3 shows a graph of the pressure as a function of time upstream of the choke 32, here the pressure in the plasma source 20, (upper curve) and the pressure downstream of the choke 32, here in the sterilization chamber 4 (lower curve). FIG. 3 shows that the pressure in the chamber 4 starts to decrease from the moment 108*a* the pump 46 is started. It is noted that the pressure upstream of the choke 32 does not decrease yet as the first and second valves 34, 38 are still closed in this example. This removes a large portion of the gasses that entered the chamber 4 while placing the medical instruments 2 therein. It will be appreciated that in the example of FIG. 3 the pump 46 can be stopped at moment 110*a*. Alternatively, a valve in a duct between the pump 46 and the chamber 4 can be closed. The first valve 34 is opened at moment 110*a*. Hence, the sterilizing mixture is fed 110 into the chamber 4 via the choke 32. Thus, the pressure in the chamber 4 will be raised by feeding the sterilizing mixture into the chamber 4 as can be seen in FIG. 3. The choke 32 in this example is dimensioned such that the pressure upstream of the choke 32 is maintained at approximately 1 bar. Hence, the pressure in the plasma source 20 can in this example not drop below a predetermined threshold pressure of approximately 1 bar. Here the flow through the choke is limited to about 10 liters per minute at 1 bar. Thereto, in this example, the choke has a round aperture of 0.785 mm.

In this example, with the first valve opened, the flow of the ionized humidified air from the plasma source 20, at least partly, recombines while flowing into the chamber 4. The sterilizing agent formed by the at least partly recombined ionized humidified air then contacts 110 the medical instruments 2 to be sterilized. Optionally, if the medical instruments 2 are, or have been, cooled, the sterilizing agent, at least partially, condenses 112 onto the medical instruments 2 and sterilizes the medical instruments 2. If the walls 6 of the chamber 4 are not cooled, less cooled than the medical instruments, or even heated, condensation of the sterilizing agent onto the walls 6 can be prevented.

In this example, as an option, the second valve 38 is opened 114 at moment 116*a* when the pressure in the chamber 4 rises to about 850 mbar, i.e. when the pressure in the chamber exceeds a predetermined threshold opening pressure of, here, 850 mbar. The opening of the second valve causes sterilizing agent to rush into the chamber 4 via the second duct 36, i.e. bypassing the choke 32. When the second valve 38 is open, the first valve 34 may be closed if desired. Hence, when the pressure in the chamber 4 is not too low, i.e. here not below the predetermined threshold opening pressure of in this example 850 mbar, the second valve 38 can be opened to allow a greater mass flow of sterilizing mixture than is achievable through the choke 32. As the pressure in the chamber 4 is above the threshold opening pressure at that time, the pressure in the plasma source cannot drop below the threshold opening pressure. Thus, greater mass flow of the sterilizing mixture is allowed without negatively affecting pressure conditions of the plasma source.

The medical instruments 2 may be taken from the chamber 116 immediately or may remain in the chamber 4 for some time for additional exposure to the sterilizing agent. The sterilizing agent may be fed to the destructor 42 via the exhaust port 14.

Figure 4:
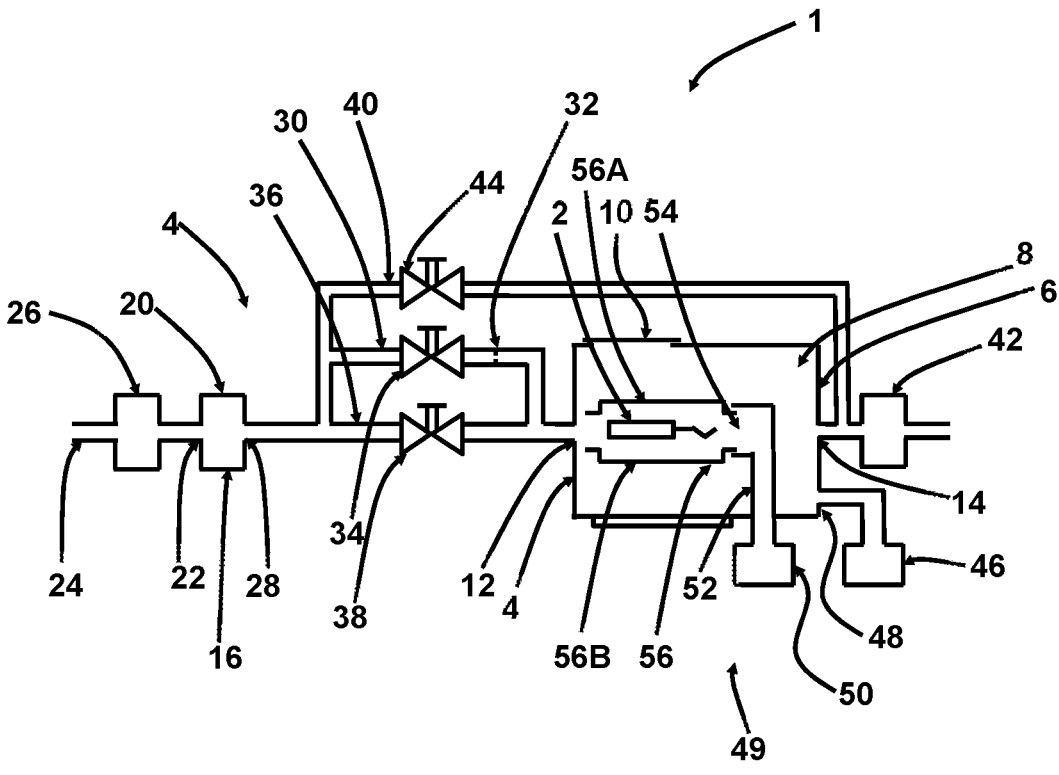
FIG. 4 shows a schematic representation of an example of an apparatus for sterilizing a medical instrument.

FIG. 4 shows a schematic representation of an example of an apparatus 1 for sterilizing a medical instrument 2. The example of FIG. 4 is similar to the example of FIG. 1. A main difference is that the apparatus 1 of FIG. 4 further includes a container 56. The container 56 is arranged for holding the medical instrument 2, here for holding a plurality of medical instruments 2. The container in this example includes a tray 56A and a lid 56B. The container 56 can be opened by removing the lid 56B from the tray 56A for placing one or more medical instruments 2 inside the container 56. The container 56 is arranged for being placed in the chamber 4. The chamber 4 can include guides for holding the container 56. The apparatus 1 in this example is arranged for opening the container inside the chamber 4. In the example of FIG. 4 the cooling unit 10 is arranged for cooling the container 56 to below the temperature of the chamber 4. Hence, the medical instruments 2 in the container 56 can easily be cooled together with the container 56. Also, hence the container 56, which can be contaminated as well, can easily be sterilized.

Figure 5:
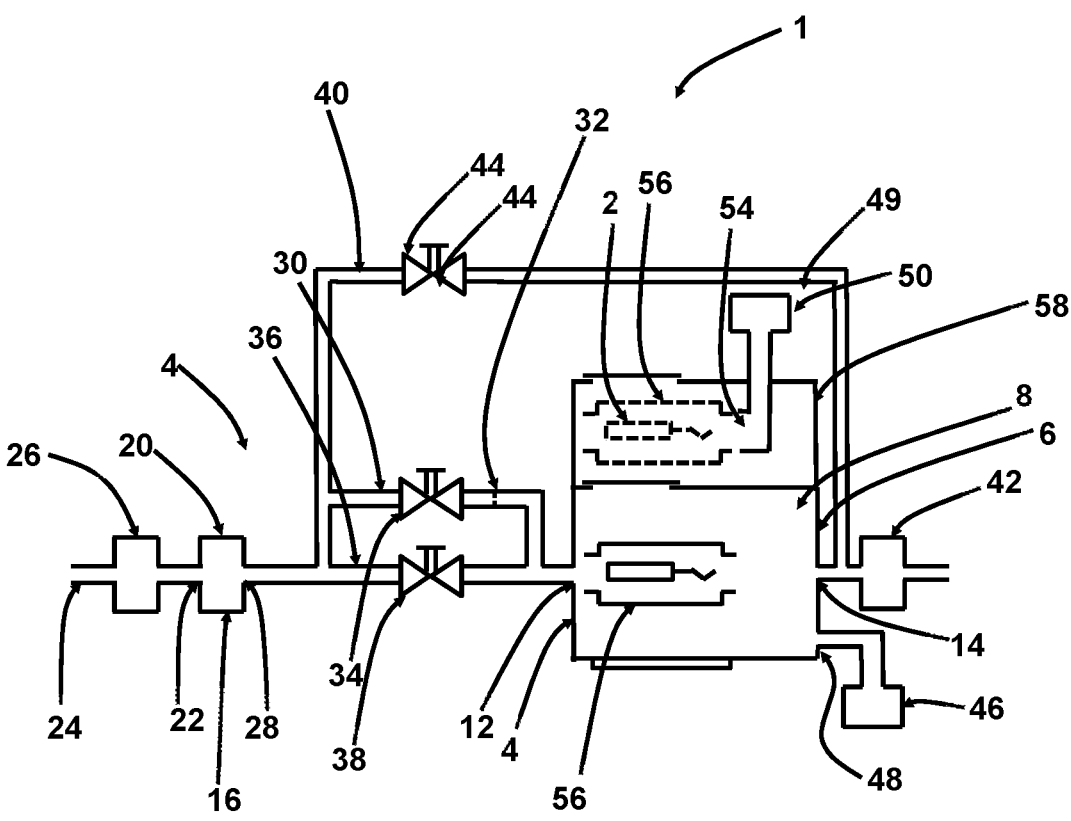
FIG. 5 shows a schematic representation of an example of an apparatus for sterilizing a medical instrument.

FIG. 5 shows a schematic representation of an example of an apparatus 1 for sterilizing a medical instrument 2. The example of FIG. 5 is similar to the example of FIG. 3. A main difference is that the apparatus 1 of FIG. 5 further includes a cooling chamber 58. The cooling chamber 58 is arranged for holding the medical instrument 2, here for holding the container 56 holding medical instruments 2 while cooling the medical instrument(s) 2 and optionally the container 56. In this example the medical instruments 2, here in the container 56, are cooled in the cooling chamber 58 and then transferred to the chamber 4 for sterilization. The apparatus 1 can include a handler unit for transferring the medical instruments 2 and/or the container 56 from the cooling chamber 58 to the sterilization chamber 4 after cooling.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

In the example of FIG. 1 the cooling unit is arranged for cooling the medical instrument in the chamber. It is also possible that alternatively, or additionally, the cooling unit is arranged for cooling the medical instrument prior to placing the medical instrument inside the chamber, e.g. as disclosed in view of FIG. 5.

It is possible that the apparatus further includes a washing unit arranged for washing and/or rinsing the medical instruments prior to sterilization. Preferably, the medical instruments are dried prior to sterilization. The cooling gas stream, optionally including the atomized water, can be supplied to the washed medical instruments for drying and cooling the medical instruments.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A device for sterilizing one or more medical instruments, including:
    a sterilizing chamber for holding the one or more medical instruments to be sterilized;
    a plasma source for providing a sterilizing mixture;
    a pressure reducer for selectively reducing pressure in the sterilizing chamber to below a pressure in the plasma source; and
    a duct for guiding the sterilizing mixture from the plasma source to the sterilizing chamber;
    wherein the duct includes a choke arranged for causing a choked flow of the sterilizing mixture from the plasma source to the chamber when the chamber is at the reduced pressure, and wherein the plasma source is an atmospheric or superatmospheric plasma source.

2. The device of claim 1, further including a bypass duct, bypassing the choke, wherein the bypass duct includes a bypass valve for being opened when the pressure in the sterilizing chamber is above a predetermined threshold opening pressure.

3. The device of claim 2, including a pressure sensor for determining the pressure in the sterilizing chamber.

4. The device of claim 2, including a controller arranged for opening the bypass valve when the pressure inside the sterilizing chamber is above the predetermined threshold opening pressure.

5. The device of claim 1, including a valve in the duct for closing the duct.

6. The device of claim 1, including a destructor arranged for destructing airborne components exiting from the sterilizing chamber.

7. A method for sterilizing one or more medical instruments, including:

providing the one or more medical instruments to be sterilized in a sterilizing chamber;

providing a plasma source for providing a sterilizing mixture;

guiding the sterilizing mixture from the plasma source to the sterilizing chamber through a duct;

preventing pressure in the plasma source from reducing below a predetermined threshold pressure by choking a flow of the sterilizing mixture from the plasma source to the sterilizing chamber;

wherein the plasma source is an atmospheric or superatmospheric plasma source.

8. The method of claim 7, including reducing a pressure in the sterilizing chamber.

9. The method of claim 8, including reducing the pressure in the sterilizing chamber while preventing the sterilizing mixture from entering the sterilizing chamber.

10. The method of claim 9, including feeding the sterilizing mixture to a destructor while reducing the pressure in the sterilizing chamber.

11. The method of claim 8, including after reducing the pressure in the sterilizing chamber, allowing the pressure in the sterilizing chamber to rise by feeding the sterilizing mixture into the sterilizing chamber via a choke.

12. The method of claim 11, including when the pressure in the sterilizing chamber exceeds a predetermined threshold opening pressure opening a bypass duct from the plasma source to the sterilizing chamber.

\* \* \* \* \*